US008452574B2

(12) United States Patent
Wilcox et al.

(10) Patent No.: US 8,452,574 B2
(45) Date of Patent: May 28, 2013

(54) SYSTEM AND METHOD OF GENERATING ATMOSPHERIC TURBULENCE FOR TESTING ADAPTIVE OPTICAL SYSTEMS

(75) Inventors: Christopher C. Wilcox, Albuquerque, NM (US); Sergio R Restaino, Albuquerque, NM (US); Ty Martinez, Edgewood, NM (US); Scott W Teare, Sorocco, NM (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 706 days.

(21) Appl. No.: 12/698,408

(22) Filed: Feb. 2, 2010

(65) Prior Publication Data

US 2010/0192709 A1  Aug. 5, 2010

Related U.S. Application Data

(60) Provisional application No. 61/149,164, filed on Feb. 2, 2009, provisional application No. 61/300,546, filed on Feb. 2, 2010.

(51) Int. Cl.
*G06F 7/60* (2006.01)
*G06F 17/10* (2006.01)

(52) U.S. Cl.
USPC ............................................................ 703/2

(58) Field of Classification Search
USPC ............... 703/2; 356/29, 300; 359/237–238
See application file for complete search history.

(56) References Cited

U.S. PATENT DOCUMENTS

2006/0024061 A1* 2/2006 Wirth et al. ............... 398/129
2006/0101106 A1* 5/2006 Subbarao .................. 708/400
2008/0140329 A1* 6/2008 Dai ............................. 702/66

OTHER PUBLICATIONS

Wilcox, C.C., Andrews, J.R., Restaino, S.R., Martinez, T., Teare, S.W., "Atmospheric Turbulence Generator Using a Liquid Crystal Spatial Light Modulator", Proceedings of the IEEE 2007 Aerospace Conference, pp. 1-8, conference date Mar. 3-10, 2007.*
Ellerbroek et al. "A Wave optics propagation code for multiconjugate adaptive optics", 2002 SPIE vol. 4494., p. 104-120.*
Zilberman, A., Golbraikh, E., Kopecki, N.S., "Propagation of electromagnetic waves in Kolmogorov and non-Kolmogorov atmospheric turbulence: three layer altitude model", Applied Optics, vol. 47, No. 34, pp. 6386-6391, Dec. 1, 2008.
Wilcox, C.C., Martinez, T., Santiago, F., Andrews, J.R., Restaino, S.R., Teare, S.W., Payne, D., "Atmospheric Turbulence Generator for Adaptive Optical Systems Testing", Advanced Wavefront Control: Methods, Devices, and Applications V, Proc. SPIE, pp. 67110D-1-67110D-9, Sep. 2007.
Ten Brummelaar, T.A., "The contribution of high order Zernike modes to wavefront tilt", Optics Communications, vol. 115, pp. 417-424, Apr. 1, 1995.

(Continued)

*Primary Examiner* — Euheen Kim
(74) *Attorney, Agent, or Firm* — Amy L. Ressing; Sally A. Ferrett

(57) ABSTRACT

A system and method for simulating atmospheric turbulence for testing optical components. A time varying phase screen representing atmospheric turbulence is generated using Karhunen-Loeve polynomials and a splining technique for generating temporal functions of the noise factor for each Zernike mode. The phase screen is input to a liquid crystal spatial light modulator. A computer display allows the user to set geometric characteristics, and select between methods for generating atmospheric turbulence including Karhunen-Loeve polynomials, Zernike polynomials, and Frozen Seeing.

19 Claims, 9 Drawing Sheets

OTHER PUBLICATIONS

Santiago, F., Wilcox, C., Chang, M., Font, C., Roura, E., Restaino, S., "Low altitude horizontal scintillation measurements of atmospheric turbulence over the sea: Experimental Results", Active and Passive Optical Components for WDM Communications V, Proc. SPIE, vol. 6014, pp. 321-329, Oct. 24, 2005.

Wilcox, C.C., Martinez, T., Santiago, F., Andrews, J.R., Restaino, S.R., Teare, S.W., Payne, D., "Atmospheric Turbulence Generator for Testing Adaptive Optical Systems ", Proc. SPIE, vol. 7015, pp. 701542-1-701542-9, conference date Jun. 23, 2008; online publication date: Aug. 12, 2008.

Wang, J.Y., Markey, J.K., "Modal compensation of atmospheric phase distortion", J. Opt. Soc. Am., vol. 68, No. 1, pp. 78-87, Jan. 1978.

Noll, R.J., "Zernike polynomials and atmospheric turbulence", J. Opt. Soc. Am., vol. 66, No. 3, pp. 207-211, Mar. 1976.

Fried, D.L., "Optical Resolution Through a Randomly Inhomogeneous Medium for Very Long and Very Short Exposures", J. Opt. Soc. Am., vol. 56, No. 10, pp. 1372-1379, Oct. 1966.

* cited by examiner

FOR KARHUNEN-LOEVE ORDER $p$ AND ZERNIKE ORDER $j$

| | | |
|---|---|---|
| $b_{1,1} = 1$ | $b_{10,17} = -0.297$ | $b_{16,71} = -0.012$ |
| $b_{2,2} = 0.999$ | $b_{10,30} = 0.050$ | $b_{17,21} = 0.910$ |
| $b_{2,7} = -0.032$ | $b_{10,47} = -0.004$ | $b_{17,34} = -0.403$ |
| $b_{2,16} = 0.002$ | $b_{11,14} = 0.935$ | $b_{17,51} = 0.095$ |
| $b_{3,3} = 0.999$ | $b_{11,25} = -0.349$ | $b_{17,72} = -0.012$ |
| $b_{3,8} = -0.032$ | $b_{11,40} = 0.069$ | $b_{18,9} = 0.254$ |
| $b_{3,17} = 0.002$ | $b_{11,64} = -0.007$ | $b_{18,18} = 0.789$ |
| $b_{4,5} = 0.984$ | $b_{12,15} = 0.935$ | $b_{18,31} = -0.537$ |
| $b_{4,12} = -0.179$ | $b_{12,26} = -0.349$ | $b_{18,48} = 0.162$ |
| $b_{4,23} = 0.019$ | $b_{12,41} = 0.069$ | $b_{18,69} = -0.027$ |
| $b_{5,6} = 0.984$ | $b_{12,65} = -0.007$ | $b_{18,94} = 0.003$ |
| $b_{5,13} = -0.179$ | | $b_{19,10} = 0.254$ |
| $b_{5,24} = 0.019$ | $b_{13,5} = 0.170$ | $b_{19,19} = 0.789$ |
| $b_{6,4} = 0.984$ | $b_{13,12} = 0.876$ | $b_{19,32} = -0.537$ |
| $b_{6,11} = -0.179$ | $b_{13,23} = -0.443$ | $b_{19,49} = 0.162$ |
| $b_{6,22} = 0.020$ | $b_{13,38} = 0.105$ | $b_{19,70} = -0.027$ |
| $b_{7,9} = 0.960$ | $b_{13,62} = -0.012$ | $b_{19,95} = 0.003$ |
| $b_{7,18} = -0.277$ | $b_{14,6} = 0.170$ | $b_{20,2} = 0.010$ |
| $b_{7,31} = 0.043$ | $b_{14,13} = 0.876$ | $b_{20,7} = 0.274$ |
| $b_{7,48} = -0.003$ | $b_{14,24} = -0.443$ | $b_{20,16} = 0.774$ |
| $b_{8,10} = 0.033$ | $b_{14,39} = 0.105$ | $b_{20,29} = -0.547$ |
| $b_{8,19} = 0.955$ | $b_{14,63} = -0.012$ | $b_{20,46} = 0.178$ |
| $b_{8,32} = -0.297$ | $b_{15,4} = 0.173$ | $b_{20,67} = -0.035$ |
| $b_{8,49} = 0.050$ | $b_{15,11} = 0.873$ | $b_{20,92} = 0.005$ |
| $b_{9,2} = 0.033$ | $b_{15,22} = -0.444$ | $b_{21,3} = 0.010$ |
| $b_{9,7} = 0.955$ | $b_{15,37} = 0.110$ | $b_{21,8} = 0.274$ |
| $b_{9,16} = -0.297$ | $b_{15,56} = 0.016$ | $b_{21,17} = 0.774$ |
| $b_{9,29} = 0.050$ | $b_{15,79} = 0.001$ | $b_{21,30} = -0.547$ |
| $b_{9,46} = -0.004$ | $b_{16,20} = 0.910$ | $b_{21,47} = 0.178$ |
| $b_{10,3} = 0.033$ | $b_{16,33} = -0.403$ | $b_{21,68} = -0.035$ |
| $b_{10,8} = 0.955$ | $b_{16,50} = 0.095$ | $b_{21,93} = 0.005$ |

ALL OTHER VALUES OF THIS $b_{p,j}$ MATRIX ARE 0

FIG. 7

SYSTEM AND METHOD OF GENERATING ATMOSPHERIC TURBULENCE FOR TESTING ADAPTIVE OPTICAL SYSTEMS

CROSS-REFERENCE TO RELATED APPLICATIONS

This Application is a nonprovisional of and claims the benefit of U.S. Provisional Application 61/149,164 filed on Feb. 2, 2009, and is a nonprovisional application of and claims the benefit of U.S. Provisional Application 61/300, 546, filed on Feb. 2, 2010. The entire disclosure of each of these documents is incorporated by reference herein.

BACKGROUND OF THE INVENTION

1. Technical Field

This application is related to systems for modeling atmospheric turbulence, and more specifically, to systems for measuring and simulating atmospheric turbulence for testing adaptive optical systems.

2. Background Information

Light traveling from a star, or any point source, will propagate spherically outward. As shown in FIG. 1, after a long distance, the wavefront, or surface of equal phase, will be flat. The Earth's atmosphere is a large, non-linear, non-homogenous medium that is constantly changing in a random fashion that affects light as it propagates through it.

When the light begins to propagate through Earth's atmosphere, the varying indices of refraction will alter the optical path, as shown in FIG. 2. The Earth's atmosphere is a non-homogeneous continuous turbulent medium, and its properties vary based on factors including temperature, pressure, wind velocities, and humidity. The Earth's atmosphere also temporally and spatially changes in a random fashion. The Kolmogorov model for atmospheric turbulence is a description of the nature of the wavefront perturbations introduced by the atmosphere and it is one of the most accepted models. It is supported by a variety of experimental measurements and is quite widely used in simulations for exo-atmospheric seeing. The Kolmogorov theory of atmospheric turbulence is based on the assumption that the turbulence varies the index of refraction and thus affects the permittivity of the medium throughout it. This affects the light as it propagates through the atmosphere.

Adaptive Optics (AO) is a term used for a class of techniques dealing with the correction of wavefront distortions in an optical system. Some wavefront distortions may include those caused by the atmosphere. Exo-atmospheric applications of adaptive optics particularly include the correction of atmospheric turbulence for a telescope system. Adaptive optics techniques are used in free space laser communication systems, high energy laser systems, and phase correction for deployable space-based telescopes and imaging systems.

Prior to deployment, an adaptive optics system requires calibration and full characterization in the laboratory. Creating realistic atmospheric simulations has been notoriously difficult, computationally intensive, and expensive. Many techniques are currently being used with adaptive optics systems for simulating atmospheric turbulence. One static component technique uses glass phase screens with holograms etched into them. Another technique uses a rotating filter wheel with etched holographic phase screens to simulate temporal transitions. However, generating and manufacturing these holograms can be quite expensive. Other methods simulate atmospheric turbulence by using a static aberrator, such as a clear piece of plastic, and rotating it, or by simply using a hot-plate directly under the beam path to cause local turbulence.

BRIEF SUMMARY OF THE INVENTION

A system and method for simulating atmospheric turbulence for testing optical components and systems. A time varying phase screen representing atmospheric turbulence is generated using Karhunen-Loeve polynomials and a splining technique for generating temporal functions of the noise factor for each mode. The phase screen is input to a liquid crystal spatial light modulator. A computer display allows the user to set geometric characteristics, and select between methods for generating atmospheric turbulence including Karhunen-Loeve polynomials, Zernike polynomials, and Frozen Seeing.

An aspect of the invention is directed to a computer implemented method for simulating atmospheric turbulence in an optical testbed system. The method includes generating a time varying wavefront representing atmospheric turbulence as input to a liquid crystal spatial light modulator. The wavefront calculated at each location and time as a weighted sum of Karhunen-Loeve polynomials and a temporal function of the noise factor generated by a spline curve fit to a sequence of random numbers, weighted with aberration amplitudes determined based on the Zernike-Kolmogorov residual errors for each Zernike mode i. The wavefront is output as a sequence of phase screens for the liquid crystal spatial light modulator. An aspect of the invention is directed to an optical testbed system for evaluating the performance of an optical component in a turbulent atmosphere. The system includes a computer processor with instructions for generating a time varying wavefront representing atmospheric turbulence and for inputting the time varying wavefront as a sequence of phase screens to a liquid crystal spatial light modulator. The wavefront is calculated at each location and time as a weighted sum of Karhunen-Loeve polynomials and a temporal function of the noise factor generated by a spline curve fit to a sequence of random numbers, weighted with aberration amplitudes determined based on the Zernike-Kolmogorov residual errors for each Zernike mode i. The system also includes a user input device for inputting user-selected variables to the computer processor, a liquid crystal spatial light modulator, an optional Fourier filter, an optical system to be tested, one or more wavefront sensors, and a computer display for displaying the wavefront output from the test unit and the reference collimated and aberrated beams.

BRIEF DESCRIPTION OF THE DRAWINGS

FIG. 7 is a table of $b_{p,j}$ values used in calculating Karhunen-Loeve polynomials.

DETAILED DESCRIPTION OF THE INVENTION

Aspects of the invention are directed to a testbed system and method that simulates atmospheric aberrations far more inexpensively and with greater fidelity using a liquid crystal spatial light modulator (LC-SLM). This system allows the simulation of atmospheric seeing conditions ranging from very poor to very good and different algorithms may be easily employed on the device for comparison. The simulations can be dynamically generated and modified very quickly and easily. The atmospheric turbulence and aberration generator described herein can be used for simulating/generating atmospheric seeing conditions, as well as generating any aberrations needed for testing an optical system.

Figure 1:
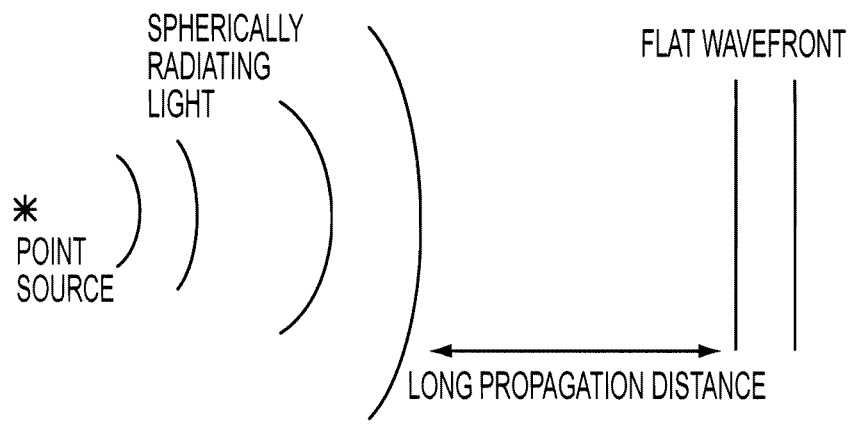
FIG. 1 illustrates propagation of a point light source over a long distance.
Figure 2:
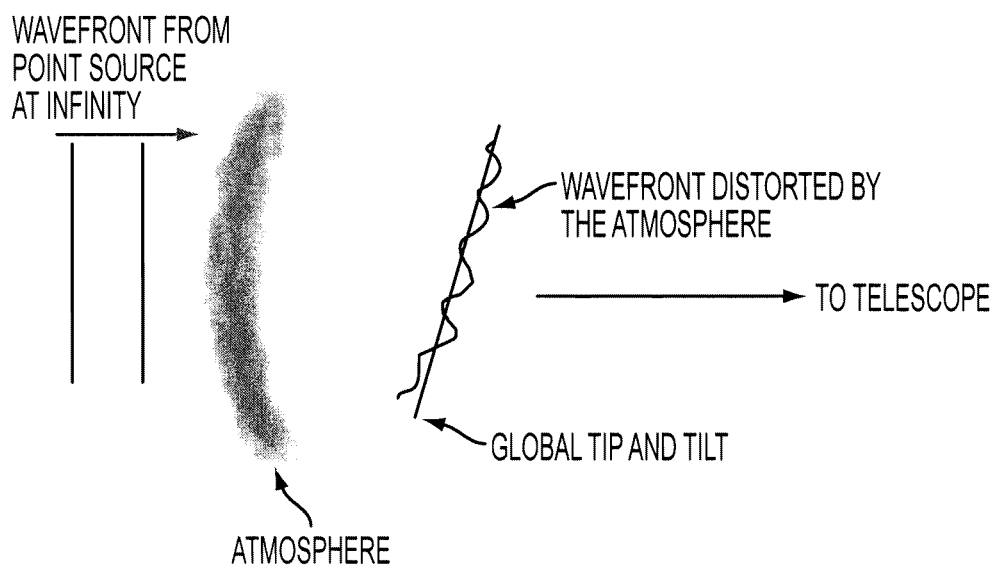
FIG. 2 illustrates distortion of a flat wavefront by the Earth's atmosphere.
Figure 3A:
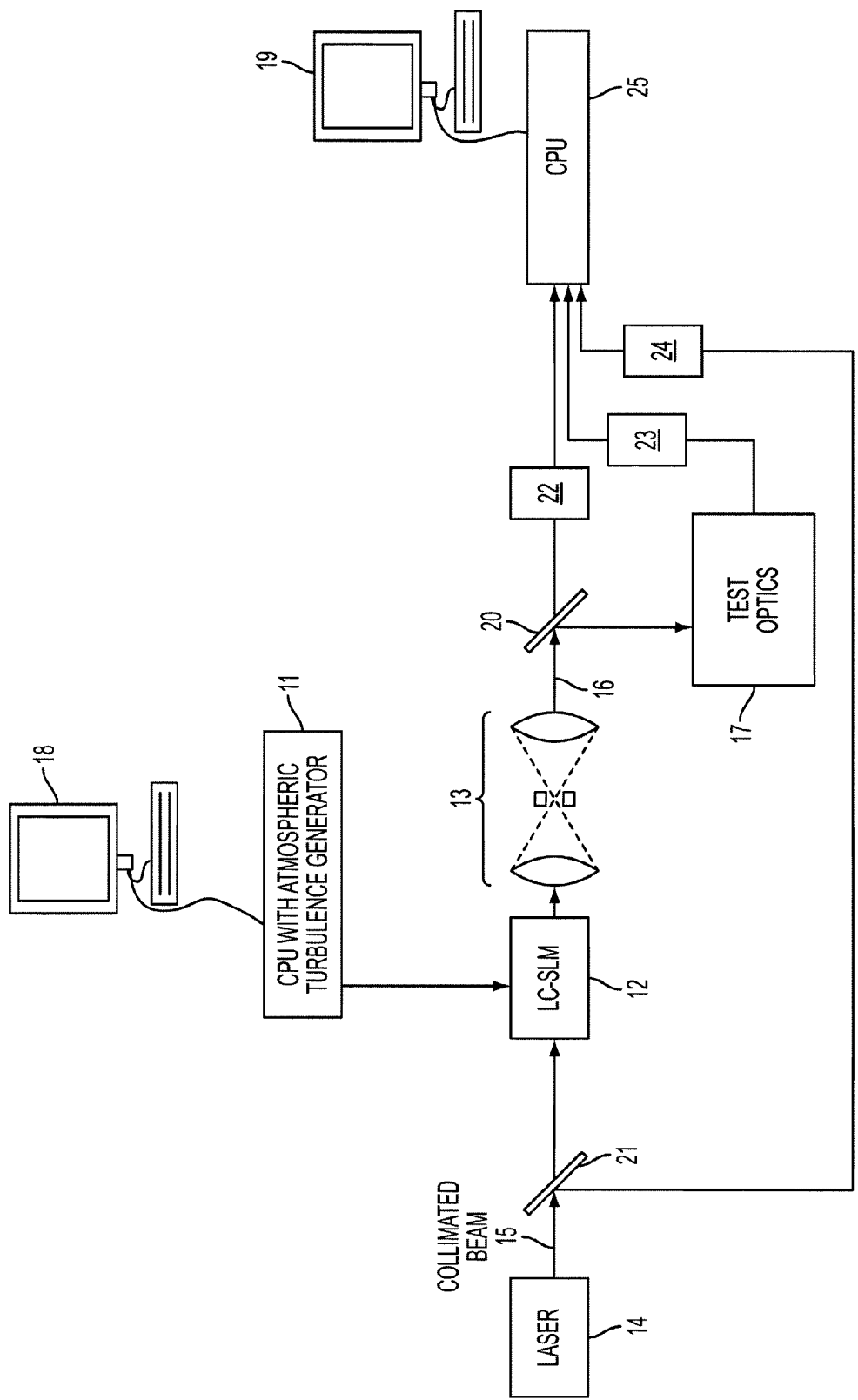
FIG. 3A is an illustration of an optical system with a liquid crystal spatial light modulator in accordance with an embodiment of the invention.
Figure 3B:
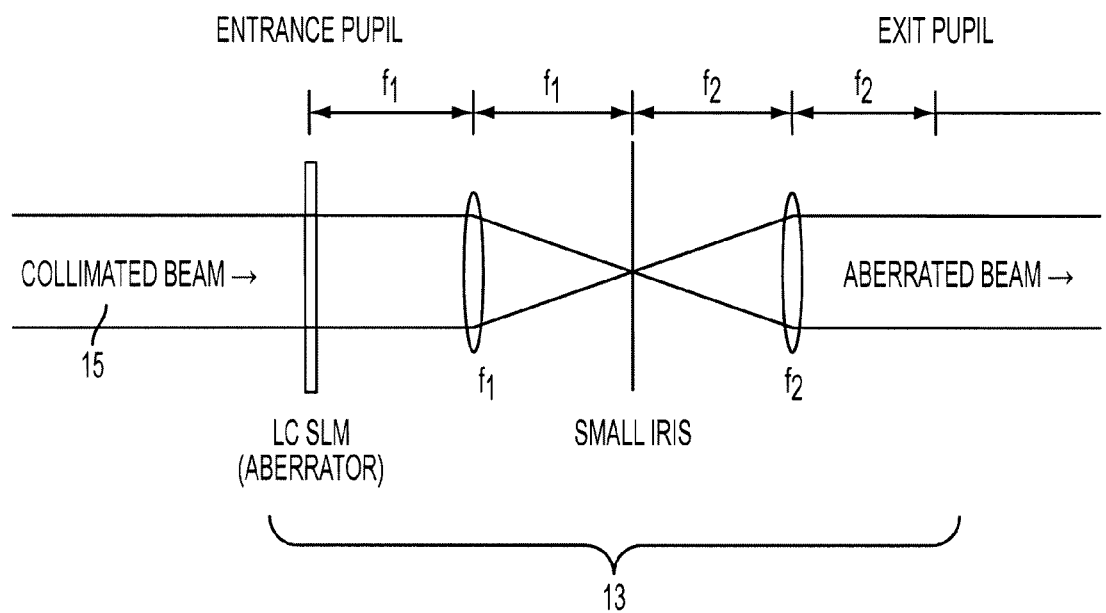
FIG. 3B illustrates the liquid crystal spatial light modulator portion of the optical system in more detail.

FIGS. 3A and 3B illustrate an optical system 10 with atmospheric turbulence generator 11 and a liquid crystal spatial light modulator 12. The liquid crystal spatial light modulator 12 receives a collimated beam from a light source such as a laser 14, and impresses an aberration on the wavefront of the collimated beam 15 from the laser 14. The aberration that is impressed on the collimated beam by the spatial light modulator 12 is generated by the atmospheric turbulence generator 11. In the exemplary embodiment described herein, the aberration is time varying, but could also be static.

The spatial light modulator 12 modulates light in amplitude and phase under computer control, allowing the phase of the wavefront to be varied across the beam.

One suitable spatial light modulator is a Holoeye spatial light modulator model LC2002 SLM manufactured by the Holoeye Corporation, headquartered in San Diego, Calif. Another spatial light modulator is available from Boulder Non-Linear Systems, headquartered in Layfayette, Colo. Other spatial light modulators can also be suitable.

Figure 4:
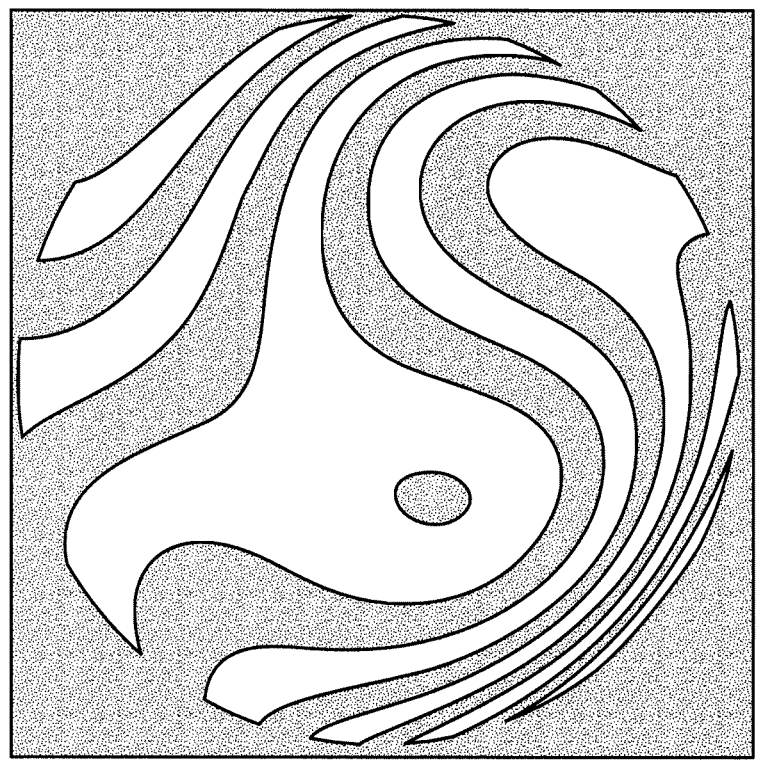
FIG. 4 shows a sample phase screen, which is a snapshot of the simulation of atmospheric turbulence.

The aberrated beam passes through an optional Fourier filter 13, as discussed further in later paragraphs, and to the optical system to be tested 17. A controller inputs the control signals to the spatial light modulator. The controller has software that places an image on the device. The image is a series of black and white bands that correspond to a phase of either 0 or $2\pi$. FIG. 4 shows a sample phase screen that can be applied to the collimated light by the spatial light modulator. The phase screen is a snapshot of the simulation of atmospheric turbulence, and has 7 or 8 fringes. The bands, or fringes, of the phase screen can also be in grayscale, with different gray values representing modulations between 0 and $2\pi$. Grayscale phase screens are suitable for use with spatial light modulators with higher resolution, e.g., high definition SLMs with resolutions of 1920×1080 pixels, or greater.

As shown in FIG. 3A, the spatial light modulator 12 is controlled by the computer system with a user input device and display 18 and computer's central processing unit with an atmospheric turbulence generator 11 programmed as instructions on the CPU.

The output of beamsplitter 21 splits the beam to measure the reference, by measuring the optical beam quality before the beam enters the LC-SLM. Beamsplitter 20 splits the beam to measure the optical beam quality after the beam has been aberrated by the LC-SLM. Then after going through the test adaptive optics system 17, the beam quality is measured to indicate how well the adaptive optics system 17 is performing. Wavefront sensors 23, 22, and 24 can be used to measure the beam quality at the output of the optical system 17 and at the output of each the beamsplitters 20 and 21, respectively. Examples of suitable wavefront sensors are Shack-Hartmann wavefront sensors, phase diversity wavefront sensors, interferometers for generating interference fringes, or simply a lens and a camera to measure the focal spot or point spread function (PSF). These methods can reconstruct the phase, with the PSF equaling the intensity pattern (e.g., the absolute value squared of the Fourier transform of the wavefront) formed from the phase (wavefront). The beam quality information from each wavefront sensor is received by the CPU 25 and displayed on the second monitor 19 and/or the control computer display screen 18.

FIG. 3B illustrates an exemplary configuration of the spatial light modulator 12 in the optical testing system of FIG. 3A in more detail. The spatial light modulator 12 is a diffractive device that can directly modulate the phase of an incoming wavefront.

The Holoeye model LC2002 SLM can modulate the phase over a range from zero to $\pi$ (pi) radians. To utilize the full $2\pi$ radian phase modulation of the incoming wavefront, a Fourier filter 13 with either a +1 or −1 diffractive order is used. The small iris in the Fourier filter allows either the +1 or the −1 diffractive order.

The Fourier filter 13 reimages the pupil for the input of the optical system under testing. The distances $f_1$ and $f_2$ are chosen to magnify or demagnify the beam size. For a spatial light modulator that only modulates 0 and $\pi$, such as the LC2002SLM, when the beam is focused, the iris blocks all the diffractive orders except the +1 or −1 order to exploit the 2× multiplicative factor in phase due to diffraction from the spatial light modulator. By using the +1 or −1 order, the phase is modulated by 0 to $2\pi$.

Note that for spatial light modulators that provide $2\pi$ modulation directly, the Fourier filter is not necessary.

The applied electrical field changes the polarization of the liquid crystal, changing the index of refraction n and the optical path length, and thus, the phase of the light passing through the SLM.

Figure 5:
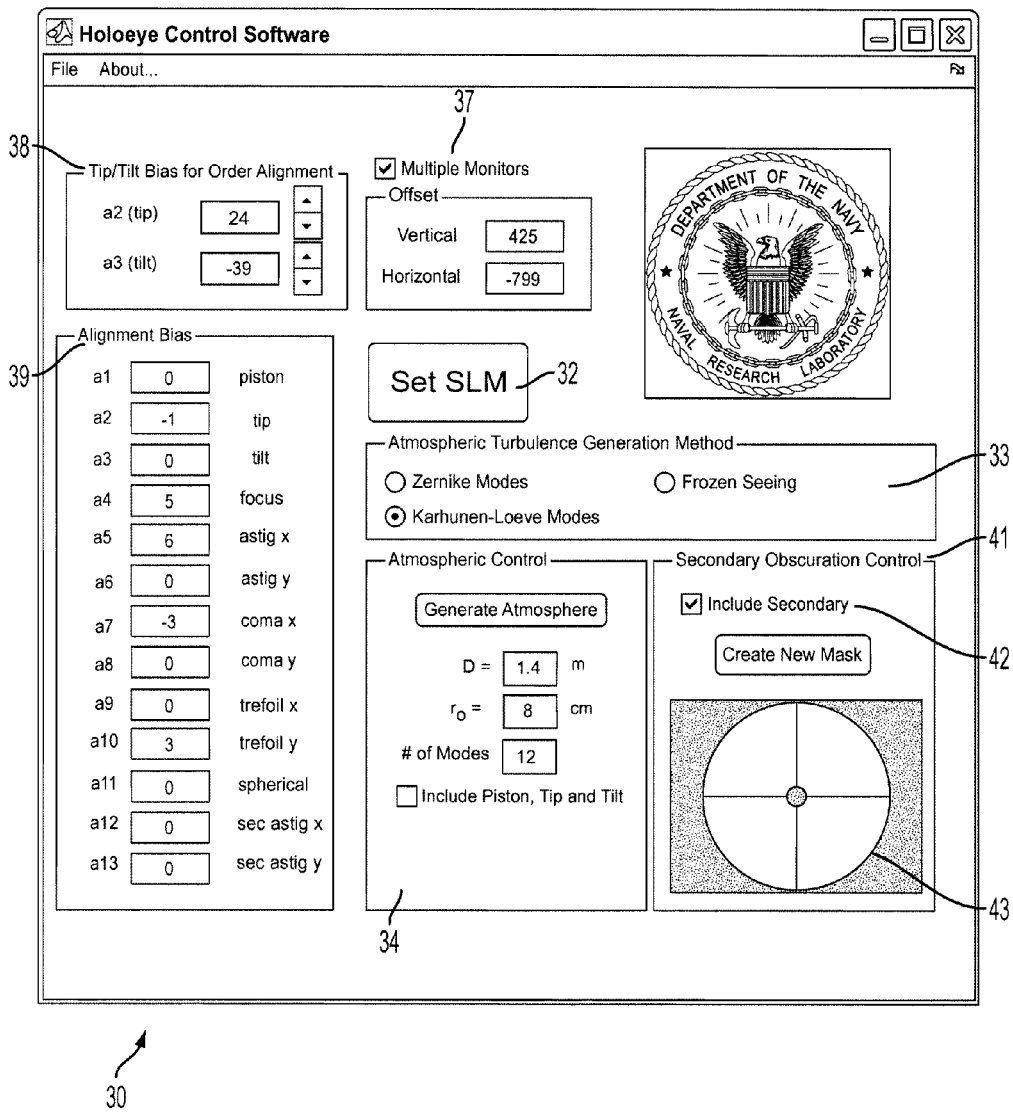
FIG. 5 shows a graphical user interface for the software that generates the phase screen for the spatial light modulator in the FIGS. 3A and 3B optical system.

FIG. 5 shows an exemplary graphical user interface (GUI) 30 for the controller software that controls the spatial light modulator. In an exemplary embodiment, the controller software is written in MATLAB.

The alignment of either the +1 or the −1 diffractive order through the small iris is done via the "tip/tilt bias for order alignment control" panel 38 in the GUI screen. Once this alignment is achieved, the user can fine-tune the alignment of the system from aberrations caused before and/or after this point in the optical path through the use of the "alignment bias" panel 39 in the GUI screen. The settings on the "tip/tilt bias for order alignment control" panel 38 are a2 (tip) and a3(tilt). The settings on the alignment bias panel 39 are a1(piston), a2(tip), a3(tilt), a4(focus), a5(astig x), a6(astig y), a7(coma x), a8(coma y), a9(trefoil x), a10(trefoil y), a11 (spherical), a12(sec astig x), and a13(sec astig y). These settings, which correspond to the first 13 Zernike modes, can compensate for aberrations in the system due to misalignments and imperfections in the system.

The software also provides the user with the option of seeing the images to be sent to the LC-SLM when no LC-SLM is connected by unchecking the "multiple monitors"

checkbox 37. The LC-SLM is connected to the computer as a second monitor, so the user can see the input parameters, the phase screen image as it changes over time, and the resulting output of the optical system to be tested. To display the LC-SLM information on the second monitor, the user clicks the "multiple monitors" checkbox 37.

The placement of the phase screen can be aligned via the Offset panel 31 by entering the vertical and horizontal values.

The user can also select between choices for determining the atmospheric turbulence generation method. The "Atmospheric turbulence generation method" panel 33 allows the user to choose between using the Zernike modes method, the Karhunen-Loeve modes method, and the Frozen Seeing method for simulating atmospheric turbulence.

Figure 6A:
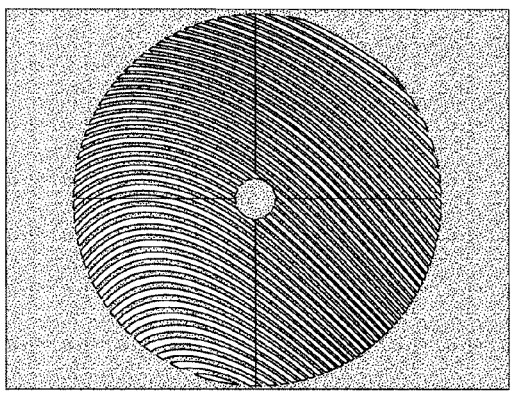
FIGS. 6A and 6B show a sample phase screen with secondary obscuration, and without secondary obscuration, respectively.
Figure 6B:
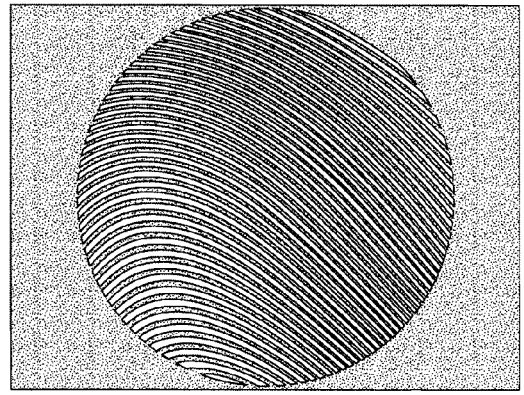

The "Secondary Obscuration Control" panel 41 allows the user to direct the software to simulate obscurations caused by a secondary mirror and its mount. Such secondary mirrors and mounts are found in telescopes and other optical systems. FIG. 6A shows a sample phase screen with a secondary obscuration. FIG. 6B shows the same sample phase screen, without a secondary obscuration. The "Include Secondary" checkbox 42 enables or disables the obscuration in the simulation. The software can include different secondary obscurations to match different mounting systems.

After a mask is created, the GUI displays an image of the mask 43.

Returning again to FIG. 5, simulating the atmosphere is set up using the "Atmospheric Control" panel 34. The user can set the desired values for the primary aperture, D, and the Fried parameter, $r_0$. The "# of Modes" box is for controlling the number of Zernike or Karhunen-Loeve modes to be used during simulations. Note that the "# of Modes" box is not used for the Frozen Seeing method of generating turbulence, as discussed further in later paragraphs.

As another option, the user can select whether or not to include the first order aberrations in the simulation by checking or unchecking the "Include Piston, Tip, and Tilt" checkbox on the User Display/Control Screen. Having this checkbox unchecked can be used to test an AO system's higher order correction abilities, as Tip and Tilt aberrations are larger in magnitude than higher modes.

Once the desired values are entered, the user can select the "Set SLM" option 32, to update the device settings.

The example Holoeye liquid crystal spatial light modulator has 800×600 pixels, and can accept a beam of 21 mm in diameter. Control of the LC-SLM can be provided via the computer's VGA (video graphics array) or DVI (digital video interface) port and the computer's graphics card.

The following discussion provides information related to the Zernike, Karhunen-Loeve, and Frozen Seeing methods for simulating atmospheric turbulence.

For a circular aperture, a generalized pupil function can be written as $$\mathbb{P}(x,y) = P(x,y)e^{(2\pi/\lambda)W(x,y)} \quad \text{Eq. (1)}$$

where $P(x, y)$ is the aperture and set as the circular function $\text{circ}(\rho)$, $\lambda$ is the wavelength, and $W(x, y)$ is the effective length error, or error in the wavefront. It is this wavefront error, $W(x, y)$, that atmospheric turbulence and aberrations induce and degrade the image quality of an optical imaging system. Aberrations can be introduced into an optical system with an LC-SLM.

The Kolmogorov model describes the nature of wavefront perturbations introduced by the Earth's atmosphere on light. The Earth's atmosphere is a large, non-linear, non-homogeneous, constantly changing medium that affects the light passing through it. The Kolmogorov model of atmospheric turbulence uses the assumption that the turbulence in the atmosphere varies the index of refraction, and thus, the permittivity of the atmosphere for light or electric fields propagating through the atmosphere.

The wavefronts to be applied to the beam can be determined based on Zernike polynomials, Karhunen-Loeve polynomials, or a frozen seeing method.

Zernike Polynomial Method

The lowest order Zernike polynomial is a uniform phase change across a wavefront, known as piston. The next-lower-order aberration is a pair known as tip and tilt, which are angular changes in the wavefront. Lower-order Zernike polynomials can be thought of as smoothly varying in phase across a wavefront. As the Zernike order increases, the phase variations over the wavefront increase on smaller spatial scales.

The following table illustrates a series of Zernike polynomials.

| \|m\|/n | 1 | 2 | 3 | 4 |
|---|---|---|---|---|
| 0 | 2r sin θ | | | |
| | 2r cos θ | | | |
| 1 | | 1.73 4r²(2r² − 1) | 2.83(3r² − 2r)sin θ | 2.236(6r² − 6r + 1) |
| | | | 2.83(3r² − 2r)cos θ | |
| 2 | | 2.4r² cos 2θ | | 3.162(4r² − 3r²)sin θ |
| | | 2.4r² sin 2θ | | 3.162(4r² − 3r²)cos θ |

The computer processor can determine the phase variations to be applied to the beam according to the following equation based on Zernike polynomials:

$$\text{Wavefront}(\rho, \theta) = \sum_i (1 + X_i)a_i Z_i(\rho, \theta) \quad \text{Eq. (2)}$$

In this equation, "Wavefront" corresponds to the $W(x, y)$ term in Equation (1) above, the Zernike modes are denoted by the index $i$, the $X_i$ values are the noise factors for the Zernike modes based on a zero-mean unitary Gaussian random distribution, and the $\alpha_i$ values are the amplitudes of the aberrations for each Zernike mode.

The Zernike polynomials $Z_i(\rho,\theta)$ are given by:
$Z_i(\rho,\theta) = \sqrt{n+1} R_n^m(\rho)\cos(\theta)$ for m≠0 and i is even;
$Z_i(\rho,\theta) = \sqrt{n+1} R_n^m(\rho)\sin(\theta)$ for m≠0 and i is odd; and $$Z_i(\rho, \theta) = R_n^0(\rho) \text{ for } m = 0, \quad \text{Eq. (3)}$$

-continued $$\text{where } R_n^m(\rho) = \sum_{s=0}^{(n-m)/2} \left[ \frac{(-1)^s (n-s)!}{s!\left(\frac{n+m}{2}-s\right)!\left(\frac{n-m}{2}-s\right)!} \rho^{n-2s} \right] \quad \text{Eq. (4)}$$

The azimuthal and radial orders of the Zernike polynomials, m and n, respectively, satisfy the conditions that m≦n and n−m=even, and i is the Zernike order number.

The Zernike polynomials have the advantage that the first few terms resemble the classical aberrations known to lens makers. The Zernike order number is related to the azimuthal and radial numbers via the numerical pattern in the following table. $\alpha_i$

| i | n | m |
|---|---|---|
| 1 | 0 | 0 |
| 2 | 1 | 1 |
| 3 | 1 | −1 |
| 4 | 2 | 0 |
| 5 | 2 | 2 |
| 6 | 2 | −2 |
| 7 | 3 | 1 |
| 8 | 3 | −1 |
| 9 | 3 | 3 |
| 10 | 3 | −3 |
| 11 | 4 | 0 |
| 12 | 4 | 2 |
| 13 | 4 | −2 |
| 14 | 4 | 4 |
| 15 | 4 | −4 |
| 16 | 5 | 1 |
| 17 | 5 | −1 |
| 18 | 5 | 3 |
| 19 | 5 | −3 |
| 20 | 5 | 5 |
| 21 | 5 | −5 |
| 22 | 6 | 0 |
| 23 | 6 | 2 |
| 24 | 6 | −2 |
| 25 | 6 | 4 |
| 26 | 6 | −4 |
| 27 | 6 | 6 |
| 28 | 6 | −6 |

The amplitudes $\alpha_i$ of Equation (2) are the coefficients of each of the Zernike modes and are calculated based on the Zernike-Kolmogorov residual errors ($\Delta_j$). The amplitude of the aberration $\alpha_i$ can be found as shown in Robert J. Noll, "Zernike polynomials and atmospheric turbulence", J. Opt. Soc. Am., Vol. 66, No. 3, March 1976, incorporated herein in its entirety. Noll calculated these Zernike coefficients $\alpha_i$ statistically and measured them experimentally. These coefficients are proportional to the residual error $\Delta_j$'s, which are related to the diameter of the aperture, D, and the Fried parameter, $r_0$.

The Zernike modes and corresponding Zernike-Kolmogorov residual errors are shown in the table below.

| Zernike mode | Zernike-Kolmogorov residual error |
|---|---|
| Tip | $\Delta_1 = 1.0299(D/r_0)^{5/3}$ |
| Tilt | $\Delta_2 = 0.5820(D/r_0)^{5/3}$ |
| Focus | $\Delta_3 = 0.1340(D/r_0)^{5/3}$ |
| Astigmatism X | $\Delta_4 = 0.0111(D/r_0)^{5/3}$ |
| Astigmatism Y | $\Delta_5 = 0.0880(D/r_0)^{5/3}$ |
| Coma X | $\Delta_6 = 0.0648(D/r_0)^{5/3}$ |
| Coma Y | $\Delta_7 = 0.0587(D/r_0)^{5/3}$ |
| Trefoil X | $\Delta_8 = 0.0525(D/r_0)^{5/3}$ |
| Trefoil Y | $\Delta_9 = 0.0463(D/r_0)^{5/3}$ |
| Spherical | $\Delta_{10} = 0.0401(D/r_0)^{5/3}$ |
| Secondary Astigmatism X | $\Delta_{11} = 0.0377(D/r_0)^{5/3}$ |
| Secondary Astigmatism Y | $\Delta_{12} = 0.0352(D/r_0)^{5/3}$ |
| Larger Orders (J > 12) | $\Delta_J = \sim 0.02944 J^{\sqrt{3}/2}(D/r_0)^{5/3}$ |

The $r_0$ term in the table above is the Fried parameter, which is the effective size of the atmospheric turbulence cells. The D term is the aperture diameter. The ratio of $r_0/D$ is important in determining whether improvements in image quality can be achieved by compensating image motion. Additional information related to the $r_0/D$ ratio is discussed in "Introduction to Image Stabilization", Scott Teare and Sergio R. Restaino, Tutorial Texts in Optical Engineering, Vol. TT73, SPIE Press, 2006, incorporated herein in its entirety.

Thus, the wavefront for a particular radius and angular location ($\rho,\theta$) is a weighted sum of the noise multiplied by the amplitude of the aberration $\alpha_i$ and the Zernike polynomial $Z_i(\rho,\theta)$. As an example, the following table shows the values of $\alpha_i$ for $D/r_0$ equal to 2.25 with the $X_i$ noise factored in:

| i | $a_i$ |
|---|---|
| 2 | 1.3423 |
| 3 | 0.3844 |
| 4 | −0.4742 |
| 5 | −1.5124 |
| 6 | 0.3981 |
| 7 | −0.2772 |
| 8 | −0.4476 |
| 9 | −0.2197 |
| 10 | 0.2499 |
| 11 | −0.0670 |
| 12 | 0.2672 |
| 13 | 0.3445 |
| 14 | −0.0917 |
| 15 | 0.0451 |
| 16 | 0.1798 |
| 17 | 0.0035 |
| 18 | −0.0103 |
| 19 | −0.1457 |
| 20 | 0.0522 |
| 21 | 0.1213 |

The term for piston, $a_1$, is neglected as a constant bias in the overall phase.

Time dependence of the generated wavefront in Equation (2) can be included as follows.

Phase variances can be described as having Gaussian random distribution, according to Tatarskii's model, in V. I. Tatarskii, Wave Propagation in a Turbulent Medium, McGraw-Hill, 1961.

Equation (2) can be written as $$\text{Wavefront}(\rho, \theta) = \sum_i (1 + X_i(t)) a_i Z_i(\rho, \theta) \quad \text{Eq. (5)}$$

Here, $X_i(t)$ are the temporal functions of the noise factor for the ith mode based on a zero-mean Gaussian random distribution. A vector of $X_i$ values is generated with a few random numbers with the zero mean unitary Gaussian distribution.

The $X_i$'s can be modified from being just random numbers, to a continuous function of time for each mode.

A spline curve, or "cubic spline data interpolation" curve, is fit to the generated vector of the few random numbers ($X_i$'s) to produce the $X_i(t)$ temporal function. The spline curve can be generated using a software package written in a commercially available software language such as MATLAB, or another computer programming language.

The software instructions include a default value for the length of time over which the simulation should be run, for example, 20 minutes, although a shorter or longer simulation time can be used. The software determines the number of random numbers Xi(t) to be generated based on the length of time for the simulation.

Karhunen-Loeve Polynomial Method

Alternatively, the computer processor can generate the wavefront using Karhunen-Loeve polynomials. The Karhunen-Loeve polynomials are statistically independent set of orthonormal polynomials. The wavefront can be generated according to the equation:

$$\text{Wavefront}(t) = \sum_i (1 + X_i(t)) a_i K_i(\rho, \theta) \qquad \text{Eq. (6)}$$

The $K_i(\rho, \theta)$ values are the Karhunen-Loeve polynomials, and are given by:

$$K_i(\rho, \theta) = \sum_{j=1}^{N} [b_{p,j} Z_j(\rho, \theta)] \qquad \text{Eq. (7)}$$

where the $b_{p,j}$ values are as calculated by Wang, J. Y. & Markey, J. K. (1978), "Modal compensation of atmospheric turbulence phase distortion," J. Opt. Soc. Am. 68, pp. 78-87, and as shown in FIG. 7. The value of N is the number of Zernike orders in which the Karhunen-Loeve order j is represented, truncated to a finite number for computation. The elements of the summation of Eq. (6) become small after a few j terms. To represent a wavefront, Equation (6) can be written as $$\text{Wavefront}(\rho, \theta) = \sum_{i=1}^{M} a_i K_i(\rho, \theta) \qquad \text{Eq (8)}$$

Here, M is the number of modes to be used in the simulation, shown in the Atmospheric Control box 34 on the GUI of FIG. 5.

The aberration $\alpha_i$ values are as described in the Zernike method above.

Here, the $X_i(t)$ values are temporal functions of the noise factor for the ith mode based on a zero-mean Gaussian random distribution. The $X_i(t)$ function in Equation (6) can be generated using random numbers described in the Zernike method above.

Figure 8:
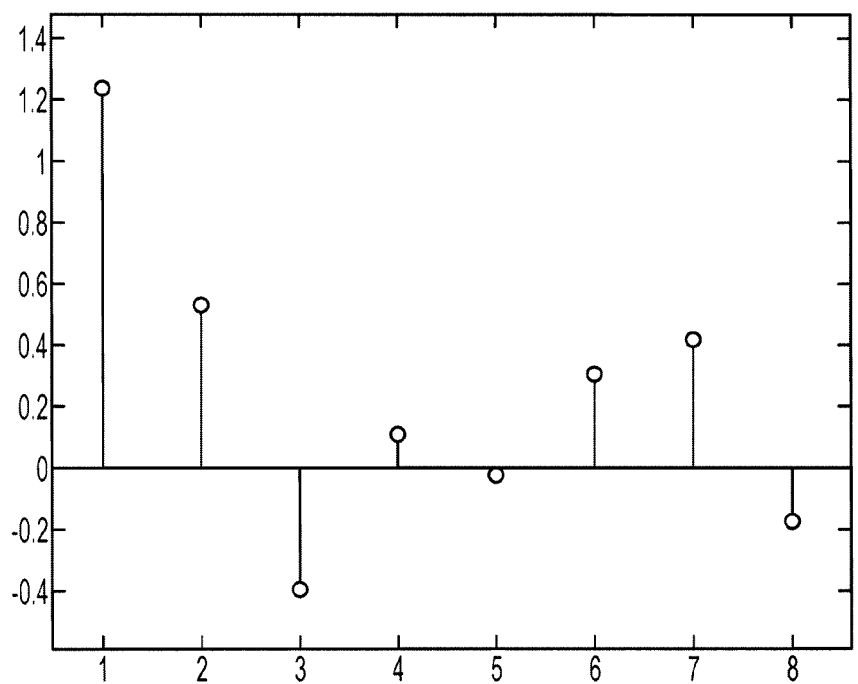
FIG. 8 illustrates an example vector with a few random numbers with the zero mean unitary Gaussian distribution for use in generating a noise function.

FIG. 8 illustrates an example vector with a few random numbers with the zero mean unitary Gaussian distribution.

Phase variances can be described as having Gaussian random distribution, according to Tatarskii's model, in V. I. Tatarskii, Wave Propagation in a Turbulent Medium, McGraw-Hill, 1961. Equation (5) can be rewritten as $$\text{Wavefront}(\rho, \theta) = \sum_i (1 + X_i) a_i K_i(\rho, \theta) \qquad \text{Eq. (9)}$$

where $X_i$ is the amount of noise for a mode i based on a zero-mean unitary Gaussian random distribution.

The $X_i$'s can be modified from being just random numbers, as shown in FIG. 8, to a continuous function of time for each mode. Equation (9) can be written as $$\text{Wavefront}(\rho, \theta) = \sum_i (1 + X_i(t)) a_i K_i(\rho, \theta) \qquad \text{Eq. (10)}$$

Figure 9:
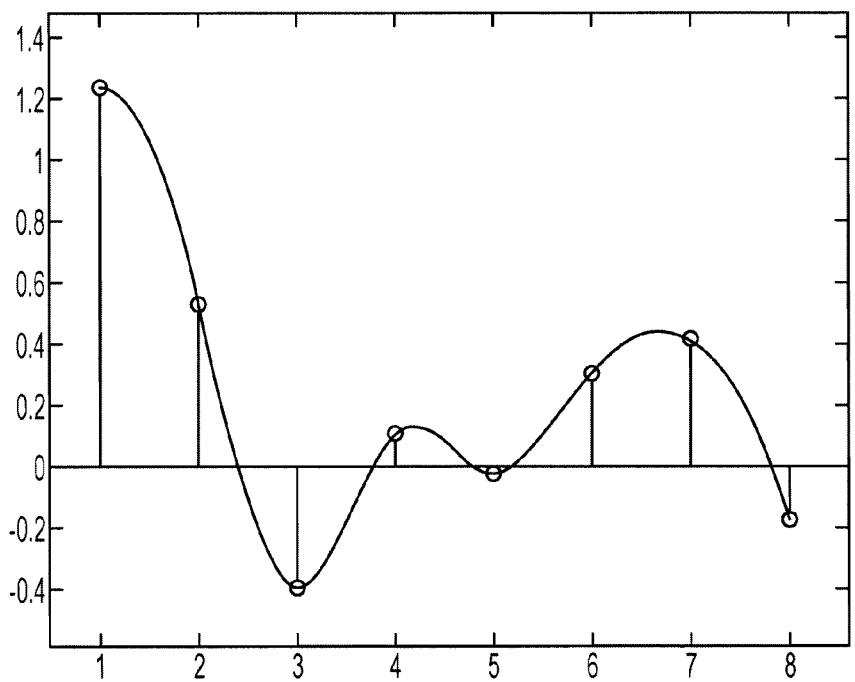
FIG. 9 illustrates a spline curve fit to the generated vector of FIG. 8.

A spline curve, or "cubic spline data interpolation" curve, is fit to the generated vector of a few random numbers ($X_i$'s) to produce the $X_i(t)$ temporal function. The spline curve can be generated using a software package written in a commercially available software language such as MATLAB, or another computer programming language. FIG. 9 shows the $X_i(t)$ as the spline curve fit to the random numbers of FIG. 8.

Note that one advantage of using a continuous function such as the spine curve is that the temporal transition of the wavefronts in the atmospheric turbulence simulation is continuous and smooth, better simulating the Earth's atmosphere as a continuously changing medium. Without using the splining technique, the change between phase screens would be discontinuous and would produce a less accurate representation of the atmosphere for testing the adaptive optics system.

The software instructions include a default value for the length of time over which the simulation should be run, for example, 20 minutes, although a shorter or longer simulation time can be used. The software determines the number of random numbers ($X_i$) to be generated based on the length of time for the simulation.

Frozen Seeing Method

The user interface of FIG. 5 also allows the user to select the Frozen Seeing method, based on the Taylor approximation, as the method of simulating temporal effects of atmospheric turbulence.

The Taylor approximation assumes that given a realization of a large portion of atmosphere, it drifts across the aperture of interest with a constant velocity determined by local wind conditions, but without any other change whatsoever. For example, a large holographic phase screen can be generated and simply moved across an aperture. This technique has proven to be a good approximation given the limited capabilities of simulating accurate turbulence conditions in a laboratory environment.

Figure 10A:
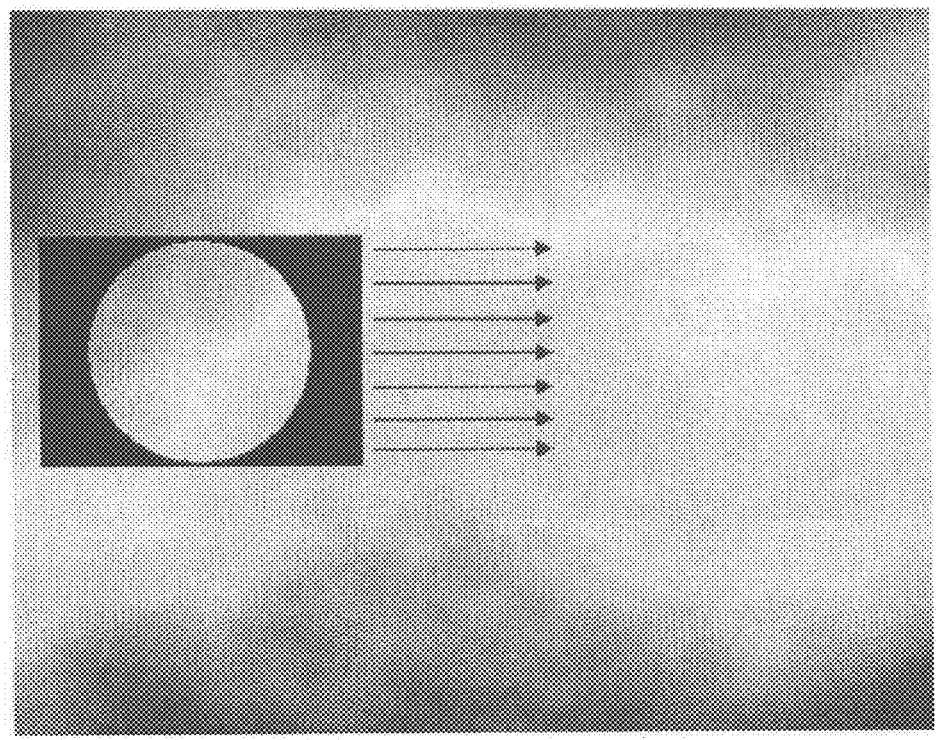
FIG. 10A illustrates a phase screen generated using a Frozen Seeing technique, showing the aperture and direction of movement.
Figure 10B:
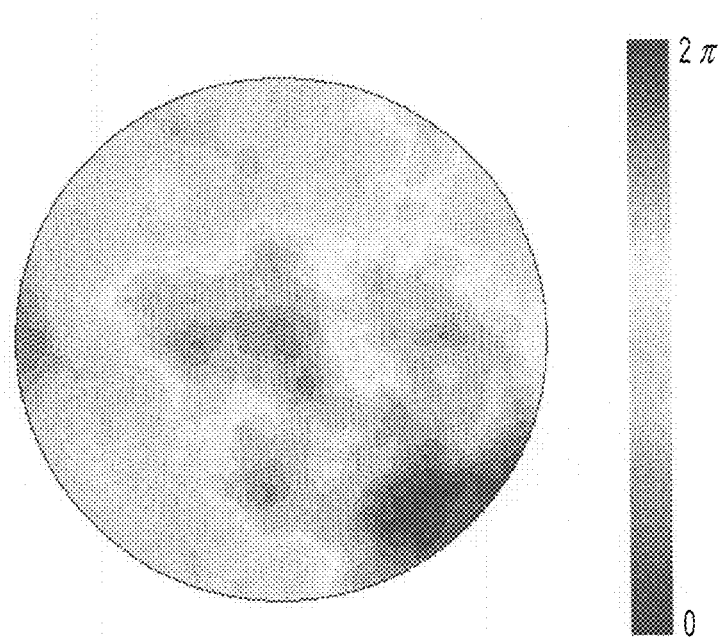
FIG. 10B shows the resulting phase screen as aligned with the aperture at a moment in time.

FIG. 10A illustrates a phase screen, showing the aperture and direction of movement. The subsection of that phase screen image aligned with the aperture represents the atmosphere at a moment in time. An example is shown in FIG. 10B. As the phase screen image is moved across the aperture, the next portion of the phase screen image that is aligned with the aperture represents the next moment in time. This process is repeated until the edge of the N×N phase screen is reached.

When the Frozen Seeing method is selected by the user, the phase screen can be generated by the computer using the Kolmogorov model, or other suitable methods.

The technique can be modified to move the phase screen in a non-linear fashion across the aperture, for example, in a circular motion, however, this can lead to an atmospheric simulation that is very repetitious.

The Frozen Seeing method is far more computationally complex than the Karhunen-Loeve or Zernike polynomial methods described above. In addition, a larger phase screen can provide a longer simulation time, however, generating a larger phase screen can be computationally intensive. For example, generating a 3000×3000 phase screen of atmosphere for the Frozen Seeing method in Matlab on a Dual Core AMD Turion X2 Ultra x64 2.2 GHz processor with 4 GB of RAM takes approximately 18 seconds. Generating a 7000×7000 phase screen takes approximately 120 seconds. Using the spline technique with the Karhunen-Loeve polynomials can produce a realistic simulation of atmospheric turbulence that lasts for longer periods of time with far less computational requirements.

The Frozen Seeing option does not require or allow the user to use some of the GUI options. For example, the user does not allow the user to input a number of modes.

Note that the color or grayscale phase screen of FIGS. 10A and 10B can be converted to a 0-$\pi$-2$\pi$ phase screen with only black and white fringes for application to a relatively low resolution LC-SLM systems. Alternatively, grayscale phase screens can be applied directly to LC-SLMs with higher resolution.

In each of the Zernike, Karhunen-Loeve, and Frozen Seeing methods, the software generates an atmospheric turbulence simulation. The phase screen generated by the software also includes modifications due to the user directed geometrical settings including tip/tilt bias and alignment bias, and due to secondary obscuration, if this feature is selected by the user. The software provides an electrical input to the LC-SLM, which spatially modulates the phase of the light passing through the LC-SLM aperture according to the phase screen.

Summary of Wavefront Generation Methods

For each of these methods, the resolution of the phase screen to be generated is set in the software for a particular model of spatial light modulator. The location and resolution for calculating the wavefront aberrations at the ($\rho,\theta$) values should correspond to the pixels of the spatial light modulator. This setting can be modified for different pixel resolutions of different spatial light modulators. For example, the Holoeye LC2002 has 800×600 pixels, a BNS spatial light modulator has 1280×1024 pixels, and a Holoeye HD SLMs has 1920×1080 pixels. Different versions of software can be stored for each model so that the right resolution is used for the corresponding device. Alternatively, the software can allow the user to select the model of SLM and the software can adjust the number and location of the ($\rho,\theta$) points accordingly.

Computer implementation of the methods described herein includes software programs with machine readable instructions for accomplishing each task. The instructions can be included in computer readable media. Hardware systems such as free space laser systems, earth or sea based telescopes, deployable space based telescopes, imaging systems including lenses and adaptive optics systems, can include modules including atmospheric turbulence simulators as described herein.

Embodiments of the invention also include methods for testing an optical system, methods for generating phase screens with a LC-SLM, and software and computer programs for implementing these methods using the techniques described herein.

Embodiments of the invention also include transforming user input to the computer system graphical user interface into a temporally changing optical wavefront using the LC-SLM.

Embodiments of the present invention may be described in the general context of computer code or machine-usable instructions, including computer-executable instructions such as program modules, being executed by a computer or other machine, such as a personal data assistant or other handheld device. Generally, program modules including routines, programs, objects, components, data structures, and the like, refer to code that performs particular tasks or implements particular abstract data types. Embodiments of the invention may be practiced in a variety of system configurations, including, but not limited to, handheld devices, consumer electronics, general purpose computers, specialty computing devices, and the like. Embodiments of the invention may also be practiced in distributed computing environments where tasks are performed by remote processing devices that are linked through a communications network. In a distributed computing environment, program modules may be located in association with both local and remote computer storage media including memory storage devices. The computer useable instructions form an interface to allow a computer to react according to a source of input. The instructions cooperate with other code segments to initiate a variety of tasks in response to data received in conjunction with the source of the received data.

Computing devices includes a bus that directly or indirectly couples the following elements: memory, one or more processors, one or more presentation components, input/output (I/O) ports, I/O components, and an illustrative power supply. Bus represents what may be one or more busses (such as an address bus, data bus, or combination thereof). One may consider a presentation component such as a display device to be an I/O component. Also, processors have memory. Categories such as "workstation," "server," "laptop," "hand held device," etc., as all are contemplated within the scope of the term "computing device."

Computing devices typically include a variety of computer-readable media. By way of example, and not limitation, computer-readable media may comprise Random Access Memory (RAM); Read Only Memory (ROM); Electronically Erasable Programmable Read Only Memory (EEPROM); flash memory or other memory technologies; CDROM, digital versatile disks (DVD) or other optical or holographic media; magnetic cassettes, magnetic tape, magnetic disk storage or other magnetic storage devices, or any other tangible physical medium that can be used to encode desired information and be accessed by computing device.

Memory includes computer storage media in the form of volatile and/or nonvolatile memory. The memory may be removable, nonremovable, or a combination thereof. Exemplary hardware devices include solid state memory, hard drives, optical disc drives, and the like. Computing device includes one or more processors that read from various entities such as memory or I/O components. Presentation component can present data indications to a user or other device. Exemplary presentation components include a display device, speaker, printing component, vibrating component, and the like.

I/O ports allow computing devices to be logically coupled to other devices including I/O components, some of which may be built in. Illustrative components include a microphone, joystick, game pad, satellite dish, scanner, printer, wireless device, etc.

The example shown in this application uses MATLAB software, although other software languages or systems are contemplated within the invention.

Obviously, many modifications and variations of the present invention are possible in light of the above teachings. It is therefore to be understood that the claimed invention may be practiced otherwise than as specifically described.

What is claimed as new and desired to be protected by Letters Patent of the United States is:

1. A computer implemented method for simulating atmospheric turbulence in an optical testbed system, the method comprising:
   generating a time varying wavefront representing atmospheric turbulence as input to a liquid crystal spatial light modulator;
   the wavefront being calculated at each location and time t as a summation, over a plurality of modes, of a product of Karhunen-Loeve polynomials, a temporal function of the noise factor generated by a spline curve fit to a sequence of random numbers, and aberration amplitudes determined based on the Zernike-Kolmogorov residual errors for each mode; and
   outputting the wavefront as a sequence of phase screens for the liquid crystal spatial light modulator.

2. The method according to claim 1, further comprising:
   applying the sequence of phase screens to the liquid crystal spatial light modulator.

3. The method according to claim 1, further comprising:
   the spatial light modulator receiving a collimated light beam, impressing the wavefront on the collimated light beam, and outputting a resulting aberrated beam to an optical system to be tested.

4. The method according to claim 1, wherein each of said modes is one of a plurality of M Zernike modes, and wherein the wavefront at the time t is calculated as $$\text{Wavefront}(t) = \sum_i (1 + X_i(t)) a_i K_i(\rho, \theta)$$

summed over i =1 to M, wherein M is a user-selected number of Zernike modes, $K_i(\rho,\theta)$ is the Karhunen-Loeve polynomial for a radius and angular location $(\rho,\theta)$ and an $i^{th}$ one of the Zernike modes, $(1+X_i(t))$ is a temporal function of the noise factor generated by a spline curve fit to a sequence of random numbers, and $a_i$ is the aberration amplitude determined based on the Zernike-Kolmogorov residual errors for the $i^{th}$ Zernike mode.

5. An optical testbed system for evaluating the performance of an optical component in a turbulent atmosphere, the system comprising:
   a computer processor with instructions for generating a time varying wavefront representing atmospheric turbulence and for inputting the time varying wavefront as a sequence of phase screens to a liquid crystal spatial light modulator;
   the wavefront being calculated at each location and time t as a weighted sum of Karhunen-Loeve polynomials and a temporal function of the noise factor generated by a spline curve fit to a sequence of random numbers, weighted with aberration amplitudes determined based on the Zernike-Kolmogorov residual errors for each Zernike mode i; and
   a user input device for inputting user-selected variables to the computer processor.

6. The system according to claim 5, wherein the user input device allows the user to select between generating the phase screen with a Zernike polynomial method, a frozen seeing method, and the Karhunen-Loeve polynomial method.

7. The system according to claim 5, wherein the user input device allows the user to input the number of modes M, the primary aperture size D, and the Fried parameter $r_0$.

8. The system according to claim 5, wherein the liquid crystal spatial light modulator has a phase modulation range of 0 to π radians, and the system further comprises:
   a Fourier filter arranged optically between the spatial light modulator and the optical system to be tested.

9. The system according to claim 5, wherein the wavefront at a radius and angular location $(\rho,\theta)$ is generated according to:

$$\text{Wavefront}(\rho, \theta) = \sum_i (1 + X_i(t)) a_i K_i(\rho, \theta),$$

wherein for each mode i, $a_i$ is the amplitude of the aberration determined based on the Zernike-Kolmogorov residual errors, $K_i(\rho,\theta)$ is the Karhunen-Loeve polynomial, and $(1+X_i(t))$ is the temporal function of the noise factor at a time t.

10. The system according to claim 5, further comprising:
    a computer screen display for displaying output light from the optical component, and a laser for directing collimated light to the spatial light modulator.

11. The system according to claim 5, wherein the optical component is a telescope.

12. The system according to claim 5, wherein the computer processor includes instructions for adding a secondary obscuration to the phase screen.

13. The optical testbed system according to claim 6, wherein the frozen seeing method includes initially generating a phase screen larger in size than an aperture of the optical system, and sequentially applying subsections of the phase screen to the spatial light modulator to simulate atmospheric turbulence.

14. A non-transitory machine readable storage medium with instructions for generating a time varying wavefront representing atmospheric turbulence and for inputting the time varying wavefront as a sequence of phase screens to a liquid crystal spatial light modulator, the instructions adapted to:
    receive user input from a user input device;
    and based on the user input, calculate a wavefront at each location and time as a weighted sum of Karhunen-Loeve polynomials and a temporal function of the noise factor generated by a spline curve fit to a sequence of random numbers, weighted with aberration amplitudes determined based on the Zernike-Kolmogorov residual errors for each mode; and
    output the wavefront to a liquid crystal spatial light modulator.

15. The machine readable storage medium according to claim 14, wherein the user input includes options of generating the phase screen with a Zernike polynomial method, a frozen seeing method, or the Karhunen-Loeve polynomial method.

16. The non-transitory machine readable storage medium according to claim 15, wherein the frozen seeing method includes initially generating a phase screen larger in size than an aperture of the optical system, and sequentially applying subsections of the phase screen to the spatial light modulator to simulate atmospheric turbulence.

17. The machine readable storage medium according to claim 14, wherein the user input includes options for a number of modes M, a primary aperture size D, and a Fried parameter $r_0$.

18. The machine readable storage medium according to claim 14, wherein the wavefront at a radius and angular location $(\rho,\theta)$ is generated according to:

$$\text{Wavefront}(\rho, \theta) \sum_i (1 + X_i(t))a_i K_i(\rho, \theta),$$

wherein for each mode i, $a_i$ is the amplitude of the aberration determined based on the Zernike-Kolmogorov residual errors, $K_i(\rho,\theta)$ is the Karhunen-Loeve polynomial, and $(1+X_i(t))$ is the temporal function of the noise factor at time t.

19. The machine readable storage medium according to claim 14, wherein the computer processor includes instructions for adding a secondary obscuration to the phase screen.

\* \* \* \* \*